(12) United States Patent
Johansen et al.

(10) Patent No.: US 11,439,625 B2
(45) Date of Patent: Sep. 13, 2022

(54) COMBINATION THERAPY FOR PROLIFERATIVE DISEASES

(71) Applicant: Avexxin AS, Trondheim (NO)

(72) Inventors: Berit Johansen, Trondheim (NO); Astrid Jullumstrø Feuerherm, Trondheim (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 16/084,832

(22) PCT Filed: Mar. 14, 2017

(86) PCT No.: PCT/EP2017/056016
§ 371 (c)(1),
(2) Date: Sep. 13, 2018

(87) PCT Pub. No.: WO2017/157951
PCT Pub. Date: Sep. 21, 2017

(65) Prior Publication Data
US 2019/0076407 A1    Mar. 14, 2019

(30) Foreign Application Priority Data
Mar. 14, 2016 (GB) ..................................... 1604318

(51) Int. Cl.
| | | |
|---|---|---|
| A61K 31/426 | (2006.01) | |
| A61K 45/06 | (2006.01) | |
| A61K 31/4745 | (2006.01) | |
| A61K 9/00 | (2006.01) | |
| A61P 35/00 | (2006.01) | |

(52) U.S. Cl.
CPC .......... *A61K 31/426* (2013.01); *A61K 9/0019* (2013.01); *A61K 31/4745* (2013.01); *A61K 45/06* (2013.01); *A61P 35/00* (2018.01)

(58) Field of Classification Search
CPC .............. A61K 31/426; A61K 31/4745; A61K 2300/00; A61K 45/06; A61P 35/00
See application file for complete search history.

(56) References Cited

U.S. PATENT DOCUMENTS

| | | |
|---|---|---|
| 3,894,152 A | 7/1975 | Pons et al. |
| 4,855,310 A | 8/1989 | Murase et al. |
| 4,902,700 A | 2/1990 | Hayasi et al. |
| 4,908,368 A | 3/1990 | Murase et al. |
| 5,177,215 A | 1/1993 | Murase et al. |
| 5,268,395 A | 12/1993 | Simandl et al. |
| 5,272,986 A | 12/1993 | Smart |
| 5,399,702 A | 3/1995 | Holland et al. |
| 5,569,655 A | 10/1996 | Dority, Jr. et al. |

(Continued)

FOREIGN PATENT DOCUMENTS

| | | |
|---|---|---|
| AU | 2006326548 A1 | 6/2007 |
| AU | 2015268638 A1 | 1/2016 |

(Continued)

OTHER PUBLICATIONS

U.S. Appl. No. 16/507,269, filed Jul. 10, 2019, Pending.
U.S. Appl. No. 16/663,931, filed Oct. 25, 2019, Pending.
U.S. Appl. No. 16/214,216, filed Dec. 10, 2018, 2019-0345168, Published.
Ge et al., Correction to Synthesis of 3-Substituted Isocoumarins via Cascade Intramolecular Ullmann-Type Coupling-Rearrangement Process. J Org Chem. 2012;77:9435.
Kokotos et al., Inhibition of group IVA cytosolic phospholipase A2 by thiazolyl ketones in vitro, ex vivo, and in vivo. J Med Chem. Sep. 25, 2014;57(18):7523-35.

(Continued)

*Primary Examiner* — Kara R McMillian
(74) *Attorney, Agent, or Firm* — McCarter & English, LLP; Steven G. Davis; Xiaoyuan (Kate) Ding

(57) ABSTRACT

A combination product comprising: (A) a compound of formula (I) (I) wherein X is O or S, preferably O; $R_6$ is H, $C_{1-6}$alkyl, —$(CH_2)_p$COOH, —$(CH_2)_p$COOC$_{1-6}$alkyl, —$(CH_2)_p$CONH$_2$, $(CH_2)_p$CONHC$_{1-6}$alkyl, and —$(CH_2)_p$CON(C$_{1-6}$alkyl)$_2$; $R^{11}$ is H or C$_{1-6}$ alkyl; each $R_5$ is —OC$_{1-10}$alkyl, —SC$_{1-10}$alkyl, —C$_{1-12}$alkyl, or OAr$^2$; wherein Ar$^2$ is phenyl, optionally substituted with one or more halo; each p is 0 to 3; each z is 1 to 2; or a salt thereof; and (B) a compound of formula (X) (X) where $R_1$ is phenyl wherein said phenyl is substituted by lower alkyl unsubstituted or substituted by cyano; $R_3$ is lower alkyl, such as methyl; and $R_4$ is quinolinyl unsubstituted or substituted by halogen; or a tautomer thereof, or a pharmaceutically acceptable salt, or a hydrate or solvate thereof.

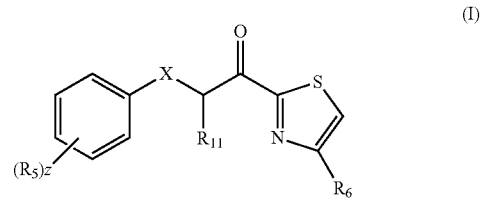

(I)

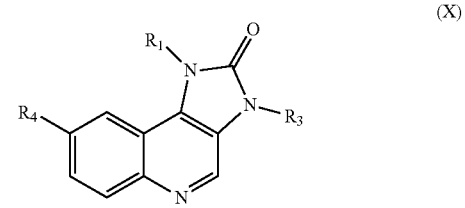

(X)

9 Claims, 1 Drawing Sheet

(56) References Cited

U.S. PATENT DOCUMENTS

| | | | |
|---|---|---|---|
| 5,569,665 A | 10/1996 | Porter et al. | |
| 5,658,909 A | 8/1997 | DeBernardis et al. | |
| 5,693,804 A | 12/1997 | DeBernardis et al. | |
| 6,214,994 B1 | 4/2001 | DeBernardis et al. | |
| 6,462,054 B1 | 10/2002 | Boger | |
| 6,753,013 B1 | 6/2004 | Didriksen et al. | |
| 7,056,917 B2 | 6/2006 | Nakayama et al. | |
| 7,667,039 B2 * | 2/2010 | Garcia-Echeverria | C07D 471/04 546/82 |
| 9,597,318 B2 | 3/2017 | Kokotos et al. | |
| 10,150,781 B2 | 12/2018 | Johansen et al. | |
| 10,259,801 B2 | 4/2019 | Johansen et al. | |
| 10,370,344 B2 | 8/2019 | Kokotos et al. | |
| 2003/0055100 A1 | 3/2003 | Uckun et al. | |
| 2003/0130340 A1 | 7/2003 | Shimada et al. | |
| 2004/0041264 A1 | 3/2004 | Kloster et al. | |
| 2005/0137243 A1 | 6/2005 | Souers et al. | |
| 2005/0272036 A1 | 12/2005 | Barton et al. | |
| 2005/0281755 A1 | 12/2005 | Zarif et al. | |
| 2005/0282792 A1 | 12/2005 | Andres | |
| 2006/0016218 A1 | 1/2006 | Shapiro et al. | |
| 2011/0053898 A1 | 3/2011 | Mehta et al. | |
| 2011/0136879 A1 | 6/2011 | Kokotos et al. | |
| 2015/0066474 A1 | 3/2015 | Yi et al. | |
| 2015/0376161 A1 | 12/2015 | Johansen et al. | |
| 2017/0166539 A1 | 6/2017 | Kokotos et al. | |
| 2017/0166589 A1 | 6/2017 | Johansen et al. | |
| 2018/0105507 A1 | 4/2018 | Johansen et al. | |
| 2019/0255023 A1 | 8/2019 | Johansen et al. | |
| 2019/0275010 A1 | 9/2019 | Johansen et al. | |
| 2019/0345168 A1 | 11/2019 | Johansen et al. | |
| 2020/0299256 A1 | 9/2020 | Johansen et al. | |

FOREIGN PATENT DOCUMENTS

| | | |
|---|---|---|
| DE | 2042504 A1 | 4/1971 |
| DE | 2063901 A1 | 7/1972 |
| EP | 0123543 A1 | 10/1984 |
| EP | 0351194 A2 | 1/1990 |
| EP | 0577003 A1 | 1/1994 |
| EP | 0735029 A1 | 10/1996 |
| EP | 0867437 A1 | 9/1998 |
| EP | 1201268 A2 | 5/2002 |
| EP | 1748044 A1 | 1/2007 |
| EP | 2116530 A1 | 11/2009 |
| GB | 1313150 A | 4/1973 |
| JP | 7-036069 | 2/1995 |
| JP | H11-509835 A | 8/1999 |
| JP | H11-255700 A | 9/1999 |
| JP | 2001-240593 A | 9/2001 |
| JP | 2002-531553 A | 9/2002 |
| JP | 2005-128778 A | 5/2005 |
| JP | 2005-343889 A | 12/2005 |
| JP | 2006-502229 A | 1/2006 |
| JP | 2006-514102 A | 4/2006 |
| JP | 2007-533621 A | 11/2007 |
| JP | 2009-527483 A | 7/2009 |
| WO | 1993/07140 A1 | 4/1993 |
| WO | 1996/03392 A1 | 2/1996 |
| WO | 1996/15792 A1 | 5/1996 |
| WO | 1996/16052 A2 | 5/1996 |
| WO | 1996/036617 A1 | 11/1996 |
| WO | 1996/39399 A1 | 12/1996 |
| WO | 1998/32741 A1 | 7/1998 |
| WO | 2000/09500 A2 | 2/2000 |
| WO | 2000/34254 A1 | 6/2000 |
| WO | 2001/00578 A1 | 1/2001 |
| WO | 2003/063878 A1 | 8/2003 |
| WO | 2004/016609 A1 | 2/2004 |
| WO | 2004/033652 A2 | 4/2004 |
| WO | 2004/041264 A1 | 5/2004 |
| WO | 2004/041269 A2 | 5/2004 |
| WO | 2005/028456 A1 | 3/2005 |
| WO | 2005/028465 A1 | 3/2005 |
| WO | 2006/016218 A1 | 2/2006 |
| WO | 2006/057503 A1 | 6/2006 |
| WO | 2006/122806 A2 | 11/2006 |
| WO | 2007/061862 A2 | 5/2007 |
| WO | 2007/070514 A1 | 6/2007 |
| WO | 2007/098142 A2 | 8/2007 |
| WO | 2008/013963 A2 | 1/2008 |
| WO | 2008/107335 A1 | 9/2008 |
| WO | 2008/150492 A1 | 12/2008 |
| WO | 2011/039365 A1 | 4/2011 |
| WO | 2012/070420 A1 | 5/2012 |
| WO | 2014/118195 A1 | 8/2014 |
| WO | 2016/016472 A1 | 2/2016 |

OTHER PUBLICATIONS

Roebrock et al., Inhibition of benzalkonium chloride-induced skin inflammation in mice by an indol-1-ylpropan-2-one inhibitor of cytosolic phospholipase A2 a. Br J Dermatol. Feb. 2012;166(2):306-16.

STN RN 927974-77-4, 4-Thiazolecarboxylic acid, 2-[2-(2,6-dimethylphenoxy)acetyl]- 3 pages, Mar. 23, 2007.

STN RN 927974-88-7, 4-Thiazolecarboxylic acid, 2-[2-(2,4-dimethylphenoxy)acetyl]-, 3 pages, Mar. 23, 2007.

STN RN 927975-43-7, 4-THiazolecarboxylic acid, 2-[2-(4-bromo-2,6-dimethylphenoxyl)acetyl]-, 3 pages, Mar. 23, 2007.

STN RN 927975-49-3, 4-Thiazolecarboxylic acid, 2-[2-(4-chloro-3-methylphenoxy)acetyl)-, 3 pages, Mar. 23, 2007.

STN RN 941685-85-4, Ethanone, 2-[(4-methoxyphenyl)methoxy]-1-[5-[7-[-[[2-(trimethylsilyl)ethoxy]methyl]-7H-pyrrolo[2,3-d]pyrimidin-4-yl]-2-thiazolyl]-, 32 pages, Jul. 9, 2007.

Yamamoto et al., Inhibitory effect of a potent and selective cytosolic phospholipase A2alpha inhibitor RSC-3388 on skin inflammation in mice. Pharmacology 2008,81(4):301-11.

International Search Report and Written Opinion for Application No. PCT/EP2017/078162, dated Dec. 22, 2017, 8 pages.

International Search Report and Written Opinion for Application No. PCT/EP2017/078169, dated Dec. 22, 2017, 8 pages.

STN RN 927975-52-8, 4-Thiazolecarboxylic acid, 2-[2-(4-clorophenoxy)acetyl], Mar. 23, 2007, 1 page.

STN RN 927975-54-0, 4-Thiazolecarboxylic acid, 2-(2-phenoxyacetyl), Mar. 23, 2007, 1 page.

STN RN 927975-57-3, 4-Thiazolecarboxylic acid, 2-[2-(2-methylphenoxy)acetyl], Mar. 23, 2007, 1 page.

STN RN 927975-60-8, 4-Thiazolecarboxylic acid, 2-[2-(2-naphthalenyloxy)acetyl], Mar. 23, 2007, 1 page.

STN RN 927975-62-0, 4-Thiazolecarboxylic acid, 2-[2-(3-methylphenoxy)acetyl], Mar. 23, 2007, 1 page.

STN RN 927975-65-3, 4-Thiazoleacetic acid, 2-[2-(4-methylphenoxy)acetyl], Mar. 23, 2007, 1 page.

STN RN 927975-68-6, 4-Thiazoleacetic acid, 2-[2-(4-ethylphenoxy)acetyl], Mar. 23, 2007, 1 page.

STN RN 927979-12-2, 4-Thiazoleacetic acid, 2-[2-(4-methoxyphenoxy)acetyl], Mar. 23, 2007, 1 page.

STN RN 927979-15-5, 4-Thiazoleacetic acid, 2-[2-(3-methoxyphenoxy)acetyl], Mar. 23, 2007, 1 page.

STN RN 927979-21-3, 4-Thiazoleacetic acid, 2-[2-[4-(1-methylethyl)phenoxy]acetyl, Mar. 23, 2007, 1 page.

STN RN 927979-27-9, 4-Thiazoleacetic acid, 2-[2-[2-(1-methylethyl)phenoxy]acetyl, Mar. 23, 2007, 1 page.

STN RN 927979-33-7, 4-Thiazoleacetic acid, 2-[2-(4-propylphenoxy)acetyl), Mar. 23, 2007, 1 page.

STN RN 927979-42-8, 4-Thiazoleacetic acid, 2-(2-(2-(1,1-dimethylethyl)phenoxyacetyl), Mar. 23, 2007, 1 page.

STN RN 927979-60-0, 4-Thiazoleacetic acid, 2-(2-[4-(1,1-dimethylpropyl)phenoxy[acetyl], Mar. 23, 2007.

STN RN 927979-82-6, 4-Thiazoleacetic acid, 2-[2-(2-ethoxyphenoxy)acetyl], Mar. 23, 2007, 1 page.

STN RN 927979-88-2, 4-Thiazoleacetic acid, 2-[2-[4-(1,1-dimethylethyl)phenoxy]acetyl, Mar. 23, 2007, 1 page.

STN RN 927979-96-2, 4-Thiazoleacetic acid, 2-(2-phenoxyacetyl), Mar. 23, 2007, 1 page.

(56) References Cited

OTHER PUBLICATIONS

STN RN 927979-98-4, 4-Thiazoleacetic acid, 2-[2-(2-methylphenoxy)acetyl], Mar. 23, 2007, 1 page.
STN RN 927980-00-5, 4-Thiazoleacetic acid, 2-[2-(2-naphthalenyloxy)acetyl], Mar. 23, 2007, 1 page.
STN RN 927980-02-7, 4-Thiazoleacetic acid, 2-[2-(3-methylphenoxy)acetyl], Mar. 23, 2007, 1 page.
Van Uitert et al., Studies on Coordination Compounds. II. The Dissociation Constants of beta-Diketones in Water-Dioxand Solutions. J Am Chem Soc., Jan. 20, 1953;75(2):455-457.
Vasudevan et al., Heterocyclic ketones as inhibitors of histone deacetylase. Bioorg Med Chem Lett. Nov. 17, 2003;13(22):3909-13.
Wen et al., Critical role of arachidonic acid-activated mTOR signaling in breast carcinogenesis and angiogenesis. Oncogene. Jan. 10, 2013;32(2):160-70.
Chinese Office Action for Application No. 201080056033.8, dated Mar. 28, 2013. 27 pages.
International Search Report and Written Opinion for Application No. PCT/EP2010/064687, dated Jan. 17, 2011. 15 pages.
International Search Report and Written Opinion for Application No. PCT/EP2015/067836, dated Sep. 23, 2015. 11 pages.
International Search Report and Written Opinion for Application No. PCT/EP2017/056016, dated May 19, 2017. 17 pages.
Ahn et al., Novel mechanistic class of fatty acid amide hydrolase inhibitors with remarkable selectivity. Biochemistry. Nov. 13, 2007;46(45):13019-30.
Allevi et al., Enzymatic Resolution of (R)-and (S)-2-(1-Hydroxyalkyl)thiazoles, Synthetic Equivalents of (R)- and (S)-2-Hydroxy Aldehydes. J Org Chem. Jun. 14, 1996;61(12):4144-4147.
Bernard et al., Palladium (0) Catalyzed Nucleophilic Substitution on 2-Cyclopropylidene-Phenoxy Ethanes. Synthetic Communications. 1997;27(5):709-723.
CAS RN 1097121-81-7, 1,3-Propanedione, 1-(2-benzothiazolyl)-3-(4-methylphenyl)-. 2 pages.
Chen, Potential value and limitation of dual inhibitors of PI3K and mTOR in the treatment of cancer. Curr Cancer Drug Targets. Feb. 2013;13(2):117-20.
Chikashita et al., General Reactivity of 2-Lithiobenzothiazole to Various Electrophiles and the Use as a Formyl Anion Equivalent in the Synthesis of alpha-Hydroxy Carbonyl Compounds. Bull Chem Soc Jpn. Oct. 1988,61:3637-3648.
Costanzo et al., Potent, small-molecule inhibitors of human mast cell tryptase. Antiasthmatic action of a dipeptide-based transition-state analogue containing a benzothiazole ketone. J Med Chem. Aug. 28, 2003;46(18):3865-76.
Doan et al., Rheumatoid arthritis: an overview of new and emerging therapies. J Clin Pharmacol. Jul. 2005;45(7):751-62.
Evans et al., Enantioselective Friedel-Crafts alkylations catalyzed by bis(oxazolinyl)pyridine-scandium(III) triflate complexes. J Am Chem Soc. Aug. 15, 2007;129(32):10029-41.
Garfunkle et al., Optimization of the central heterocycle of alpha-ketoheterocycle inhibitors of fatty acid amide hydrolase. J Med Chem. Aug. 14, 2008;51(15):4392-403.
Gautam et al., Identification of selective cytotoxic and synthetic lethal drug responses in triple negative breast cancer cells. Mol Cancer. May 10, 2016;15(1):34. 16 pages.
Golub et al., Molecular classification of cancer: class discovery and class prediction by gene expression monitoring. Science. Oct. 15, 1999;286(5439):531-7.
Hua et al., AKT and cytosolic phospholipase A2a form a positive loop in prostate cancer cells. Curr Cancer Drug Targets. 2015;15(9):781-91.
Kraus et al., Halogen-Metal Exchange/Cyclization of Iodoketones: A Direct Synthesis of 3-Arylbenzofurans. Synlett. 2005;16:2504-2506.
Maira et al., Identification and characterization of NVP-BEZ235, a new orally available dual phosphatidylinositol 3-kinase/mammalian target of rapamycin inhibitor with potent in vivo antitumor activity. Mol Cancer Ther. Jul. 2008;7(7):1851-63.

Marsilje et al., Design, synthesis, and biological evaluation of simplified alpha-keto heterocycle, trifluoromethyl ketone, and formyl substituted folate analogues as potential inhibitors of GAR transformylase and AICAR transformylase. Bioorg Med Chem. Oct. 1, 2003;11(20):4487-501.
Martin et al., Highly efficient borylation Suzuki coupling process for 4-bromo-2-ketothiazoles: straightforward access to micrococcinate and saramycetate esters. Org Lett. Aug. 20, 2009;11(16):3690-3. Supporting Information.
Maryanoff et al., Inhibitors of proteases and amide hydrolases that employ an alpha-ketoheterocycle as a key enabling functionality. Bioorg Med Chem. Feb. 15, 2008;16(4):1562-95.
McGrath et al., Structure-guided design of peptide-based tryptase inhibitors. Biochemistry. May 16, 2006,45(19):5964-73.
Mete et al., Design of novel and potent cPLA2a inhibitors containing an a-methyl-2-ketothiazole as a metabolically stable serine trap. Bioorg Med Chem Lett. May 15, 2011;21(10):3128-33.
Myllymäki et al., Design, synthesis, and in vitro evaluation of carbamate derivatives of 2-benzoxazolyl- and 2-benzothiazolyl-(3-hydroxyphenyl)-methanones as novel fatty acid amide hydrolase inhibitors. J Med Chem. Aug. 23, 2007;50(17):4236-42.
PubChem CID 9159507, AC1PLZGU, Oct. 8, 2016, 10 pages.
Reid et al., Notiz Uber Heterocyclisch Substituierte Pyrazoline. European Journal of Inorganic Chemistry. Nov. 1957;90(11):2707-2711.
Ricci et al., Heteroacylsilanes: synthesis and synthetic potentialities of new nucleophilic acylation agents. J Org Chem. Jan. 1985;50(1):130-133.
Schmidt et al., Amino Acids and Peptides; 581 Synthesis of Optically Active 2-(1-Hydroxyalkyl)-thiazole-4-carboxylic Acids and 2-(1-Aminoalkyl)-thiazole-4-carboxylic Acids. Synthesis. 1986;12:992-998.
Sierstad et al., Discovery and development of fatty acid amide hydrolase (FAAH) inhibitors. J Med Chem. Dec. 11, 2008;51(23):7327-43.
STN RN 10471-74-6, 1,3-Propanedione, 1-phenyl-3-(2-thienyl), Nov. 16, 1984, 1 page.
STN RN 1094445-68-7, 1,3-Propanedione, 1-(2-benzothiazolyl)-3-phenyl, Jan. 20, 2009, 1 page.
STN RN 1179358-89-4, 1-Propanone, 3-phenyl-1-(2-thiazolyl), Sep. 2, 2009, 1 page.
STN RN 1347363-73-8, Ethanone, 2-phenoxy-1-[6-(1H-pyrazol-4-yl)-2-benzothiazolyl], Dec. 2, 2011, 1 page.
STN RN 374754-17-3, Ethanone, 2-[(3-methoxyphenyl)thio]-1-(2-thiazolyl), Dec. 12, 2001, 1 page.
STN RN 82605-58-1, 1-Propanone, 1,3-bis(2-benzothiazolyl), Nov. 16, 1984, 1 page.
STN RN 882284-72-2, 2-Thiopheneacetic acid, 5-[2-(phenylthio)acetyl], Apr. 30, 2006, 1 page.
STN RN 927974-68-3, 4-Thiazolecarboxylic acid, 2-[2-(4-methylphenoxy)acetyl], Mar. 23, 2007, 1 page.
STN RN 927974-71-8, 4-Thiazolecarboxylic acid, 2-[2-(4-,ethylphenoxy)acetyl], Mar. 23, 2007, 1 page.
STN RN 927974-82-1, 4-Thiazolecarboxylic acid, 2-[2-(2,3-dimethylphenoxy)acetyl], Mar. 23, 2007, 1 page.
STN RN 927974-85-4, 4-Thiazolecarboxylic acid, 2-[2-(3,4-dimethylphenoxy)acetyl], Mar. 23, 2007, 1 page.
STN RN 927974-91-2, 4-Thiazolecarboxylic acid, 2-[2-(4-methoxyphenoxy)acetyl], Mar. 23, 2007, 1 page.
STN RN 927974-94-5, 4-Thiazolecarboxylic acid, 2-[2-(3-methoxyphenoxy)acetyl], Mar. 23, 2007, 1 page.
STN RN 927974-99-0, 4-Thiazolecarboxylic acid, 2-[2-[4-{1-methylethyl)phenoxy]acetyl], Mar. 23, 2007, 1 page.
STN RN 927975-03-9, 4-Thiazolecarboxylic acid, 2-[2-[2-{1-methylethyl)phenoxy]acetyl], Mar. 23, 2007, 1 page.
STN RN 927975-07-3, 4-Thiazolecarboxylic acid, 2-[2-(4-propylphenoxy)acetyl], Mar. 23, 2007, 1 page.
STN RN 927975-11-9, 4-Thiazolecarboxylic acid, 2-[2-[3-methyl-4-(1-methylethyl)phenoxy]acetyl], Mar. 23, 2007, 1 page.
STN RN 927975-13-1, 4-Thiazolecarboxylic acid, 2-[2-[2-(1,1-dimethylethyl)phenoxy]acetyl], Mar. 23, 2007, 1 page.
STN RN 927975-25-5, 4-Thiazolecarboxylic acid, 2-[2-[4-(1,1-dimethylpropyl)phenoxy]acetyl], Mar. 23, 2007, 1 page.

(56) References Cited

OTHER PUBLICATIONS

STN RN 927975-29-9, 4-Thiazolecarboxylic acid, 2-[2-[2-(1,1-dimethylethyl)-4, Mar. 23, 2007, 1 page.
STN RN 927975-33-5, 4-Thiazolecarboxylic acid, 2-[2-[4-(1-methyl-1-phenylethyl)phenoxy)acetyl], Mar. 23, 2007, 1 page.
STN RN 927975-39-1, 4-Thiazolecarboxylic acid, 2-[2-([1,1'-biphenyl1-4-yloxy)acetyl), Mar. 23, 2007, 1 page.
STN RN 927975-41-5, 4-Thiazolecarboxylic acid, 2-[2-(2-ethoxyphenoxy)acetyl], Mar. 23, 2007, 1 page.
STN RN 927975-47-1, 4-Thiazolecarboxylic acid, 2-[2-[4-(1,1-dimethylethyl)phenoxy]acetyl], Mar. 23, 2007, 1 page.
U.S. Appl. No. 12/897,510, filed Oct. 4, 2010, U.S. Pat. No. 9,597,318, Issued.
U.S. Appl. No. 15/442,568, filed Feb. 24, 2017, U.S. Pat. No. 10,370,344, Issued.
U.S. Appl. No. 16/507,269, filed Jul. 10, 2019, Abandoned.
U.S. Appl. No. 14/764,509, filed Jul. 29, 2015, 2015-0376161, Abandoned.
U.S. Appl. No. 15/789,834, filed Oct. 20, 2017, U.S. Pat. No. 10,259,801, Issued.
U.S. Appl. No. 16/294,159, filed Mar. 6, 2019, Abandoned.
U.S. Appl. No. 16/663,931, filed Oct. 25, 2019, 2020-0299256, Allowed.
U.S. Appl. No. 15/501,141, filed Feb. 1, 2017, U.S. Pat. No. 10,150,781, Issued.
U.S. Appl. No. 16/214,216, filed Dec. 10, 2018, U.S. Pat. No. 10,851,114, Issued.
U.S. Appl. No. 17/076,554, filed Oct. 21, 2020, Pending.
U.S. Appl. No. 16/347,253, filed May 3, 2019, 2019-0255023, Published.
U.S. Appl. No. 16/347,256, filed May 3, 2019, 2019-0275010, Published,
Brachmann et al., Specific apoptosis induction by the dual PI3K/mTor inhibitor NVP-BEZ235 in HER2 amplified and PIK3CA mutant breast cancer cells. Proc Natl Acad Sci U S A. Dec. 29, 2009;106(52):22299-304.

* cited by examiner

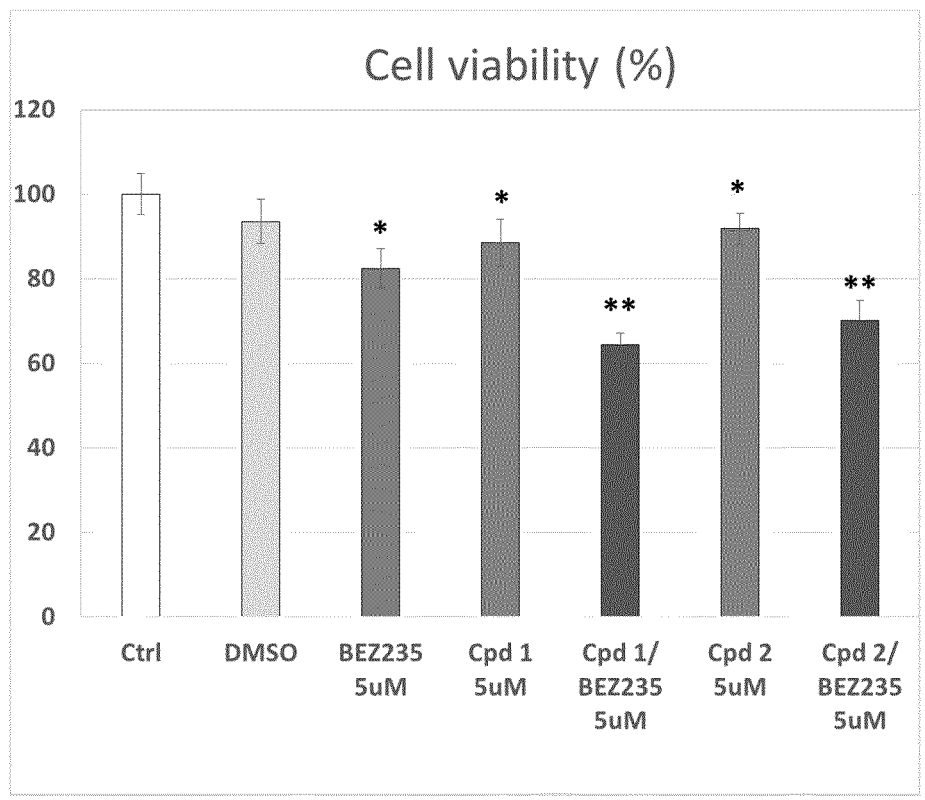

COMBINATION THERAPY FOR PROLIFERATIVE DISEASES

CROSS-REFERENCE TO RELATED APPLICATIONS

This application is a 35 U.S.C. § 371 national stage application of International Application No. PCT/EP2017/056016, filed Mar. 14, 2017, which claims priority to United Kingdom Patent Application No. 1604318.4, filed Mar. 14, 2016.

This invention relates to a pharmaceutical composition or combination product comprising certain thiazole derivatives in combination with certain protein kinase inhibitors, in particular phosphatidylinositol-4,5-bisphosphate 3-kinase inhibitors (PI3K) and more particularly dual inhibitors of PI3K and mammalian target of rapamycin (mTOR). The invention also relates to the use of said pharmaceutical composition or combination product for the treatment or prevention of proliferative conditions such as cancer, e.g. breast cancer. The invention also relates to methods of treating or preventing proliferative conditions in patients comprising administration of the pharmaceutical composition or combination product of the invention to the patient.

BACKGROUND

Basal-like breast cancer (BLBC), which represents ~15% of all breast cancers, is an aggressive molecular subtype of the disease associated with poor prognosis. Most BLBCs are triple-negative (lacking expression of estrogen receptor, progesterone receptor, and human epidermal growth factor receptor 2) and thus unresponsive to currently available targeted therapies. Hence, new molecular targets for treatment are called for.

The present inventors have devised a new combination therapy that targets proliferative conditions in general and breast cancer in particular.

The invention relies on the combination of a certain thiazole compounds and a specific dual inhibitor of PI3K and mTOR. The present inventors have surprisingly found that the combination of these two compounds leads to a combination therapy that works synergistically. In particular, the combination has been shown to synergistically reduce breast cancer cell viability.

SUMMARY OF INVENTION

Thus, viewed from one aspect the invention provides a pharmaceutical composition comprising:
(A) A Compound of Formula (I):

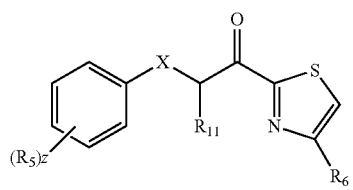

(I)

wherein X is O or S, preferably O
$R_6$ is H, $C_{1-6}$alkyl, $—(CH_2)_p COOH$, $—(CH_2)_p COOC_{1-6}$alkyl, $—(CH_2)_p CONH_2$, $—(CH_2)_p CONHC_{1-6}$alkyl, and $—(CH_2)_p CON(C_{1-6}alkyl)_2$;
$R^{11}$ is H or $C_{1-6}$ alkyl;
each $R_5$ is $—OC_{1-10}$alkyl, $—SC_{1-10}$alkyl, $—C_{1-12}$alkyl, or $OAr^2$;
wherein $Ar^2$ is phenyl, optionally substituted with one or more halo;
each p is 0 to 3;
each z is 1 to 2;
or a salt thereof;
(B) A Compound of Formula (X)

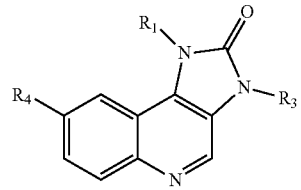

(X)

where $R_1$ is phenyl wherein said phenyl is substituted by lower alkyl unsubstituted or substituted by cyano;
$R_3$ is lower alkyl, such as methyl; and
$R_4$ is quinolinyl unsubstituted or substituted by halogen;
or a tautomer thereof, or a pharmaceutically acceptable salt, or a hydrate or solvate thereof.

Viewed from another aspect the invention provides a combination product for simultaneous, sequential or separate use comprising:
(A) a Compound of Formula (I):

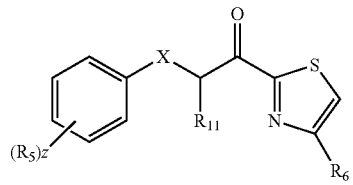

(I)

wherein X is O or S, preferably O
$R_6$ is H, $C_{1-6}$alkyl, $—(CH_2)_p COOH$, $—(CH_2)_p COOC_{1-6}$alkyl, $—(CH_2)_p CONH_2$, $—(CH_2)_p CONHC_{1-6}$alkyl, and $—(CH_2)_p CON(C_{1-6}alkyl)_2$;
$R^{11}$ is H or $C_{1-6}$ alkyl;
each $R_5$ is $—OC_{1-10}$alkyl, $—SC_{1-10}$alkyl, $—C_{1-12}$alkyl, or $OAr^2$;
wherein $Ar^2$ is phenyl, optionally substituted with one or more halo;
each p is 0 to 3;
each z is 1 to 2;
or a salt thereof
and
(B) A Compound of Formula (X)

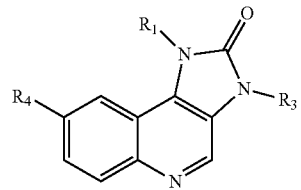

(X)

where $R_1$ is phenyl wherein said phenyl is substituted by lower alkyl unsubstituted or substituted by cyano;
$R_3$ is lower alkyl, such as methyl; and
$R_4$ is quinolinyl unsubstituted or substituted by halogen; or a tautomer thereof, or a pharmaceutically acceptable salt, or a hydrate or solvate thereof.

Viewed from another aspect the invention provides a pharmaceutical kit composition for simultaneous, sequential or separate use comprising a first composition comprising a compound (I) as herein defined and a pharmaceutically-acceptable diluent or carrier, and a second composition comprising a compound (X) as herein defined and a pharmaceutically-acceptable diluent or carrier.

In particular, the invention relates to a pharmaceutical composition, combination product or kit as herein before defined in which the compound of formula (I) is:

Compound 1

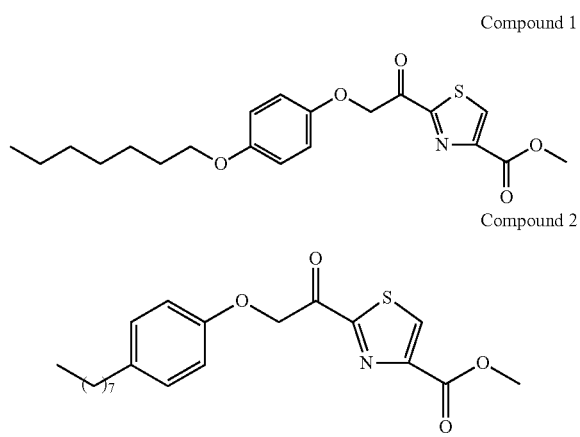

Compound 2 or a salt thereof; and
the compound of formula (X) is

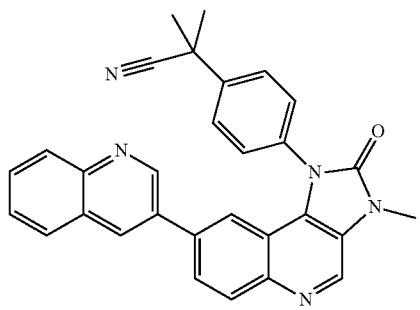 [SMILES: Cn1c(=O)n(-c2ccc(C(C)(C)C#N)cc2)c2c3cc(-c4cnc5ccccc5c4)ccc3ncc21]

or a salt thereof.

Viewed from another aspect the invention provides a pharmaceutical composition or combination product as hereinbefore defined for use in the treatment or prevention of a proliferative disorder such as cancer, especially breast carcinoma.

Viewed from another aspect the invention provides a method of treating, such as reducing symptoms of, or preventing a proliferative disorder such as cancer, especially breast carcinoma in a patient in need thereof comprising administering to said patient, preferably a human, an effective amount of a composition or combination product as herein before defined.

Viewed from another aspect the invention provides a method of treating, such as reducing symptoms of, or preventing a proliferative disorder such as cancer, especially breast carcinoma in a patient in need thereof comprising administering to said patient, preferably a human, an effective amount of a compound of formula (I) and simultaneously, separately or sequentially administering to said patient a compound of formula (X) as herein before defined. In sequential administration either compound can be administered first.

Viewed from another aspect the invention provides a method of treating, such as reducing symptoms of, or preventing a proliferative disorder such as cancer, especially breast carcinoma, in a patient in need thereof comprising:
(i) identifying a patient who has received either a compound of formula (I) or a compound of formula (X) as herein before defined respectively;
(ii) administering to said patient an effective amount of either a compound of formula (X) or a compound of formula (I) as herein before defined so that said patient is administered with both a compound of formula (I) and a compound of formula (X).

Viewed from another aspect the invention provides use of a composition or combination product as hereinbefore defined in the manufacture of a medicament for treating, such as reducing symptoms of, or preventing a proliferative disorder such as cancer, especially breast carcinoma.

Viewed from another aspect the invention provides a process for the preparation of a composition as hereinbefore defined comprising blending a compound of formula (I) and a compound of formula (X) in the presence of at least one pharmaceutical excipient.

Definitions

The term lower alkyl is used herein to refer to C1-6 alkyl groups, preferably C1-4 alkyl groups, especially C1-3 alkyl groups. These alkyl groups can be linear or branched, preferably linear.

The invention relates both to a pharmaceutical composition in which compounds (I) and (X) are blended together in a single composition and to a combination product such as a kit in which the active compounds are provided in separate compositions but are designed for administration simultaneously, separately or sequentially. Any method for treating or preventing a proliferative disorder as defined herein encompasses simultaneous, separate or sequential administration of the active components or administration of the composition of the invention.

A "combination" according to the invention refers to either a fixed combination in one dosage unit form, or a kit of parts for the combined administration where a compound of the formula (I) and its combination partner formula (X)(also referred to as "combination partner" or "therapeutic agent") may be administered independently at the same time or separately within time intervals, especially where these time intervals allow that the combination partners show a cooperative and preferably a synergistic effect.

A "combination product" as used herein means a product suitable for pharmaceutical use that results from the mixing or combining of more than one active ingredient and includes both fixed and non-fixed combinations of the active ingredients. The term "fixed combination" or "fixed dose" means that the active ingredients, e.g. a compound of formula (I) and its combination partner formula (X), are both administered to a patient simultaneously in the form of a single entity or dosage. The term "non-fixed combination" means that the active ingredients, e.g. a compound of formula (I) and the combination partner formula (X) are both administered to a patient as separate entities either simultaneously, concurrently or sequentially with no specific time limits, wherein such administration provides therapeutically effective levels of the two compounds in the body of the warm-blooded animal in need thereof.

All discussion below relating to preferred compounds of the invention is equally applicable to both these aspects of the invention.

DETAILED DESCRIPTION

This invention concerns a combination therapy of a compound of formula (I) and a compound of formula (X). We have surprisingly found that this combination therapy results in synergy. Our results demonstrate a reduction in the viability of breast cancer cells, the composition or combination product offering a larger reduction than could have been expected from the use of individual compounds individually, i.e. the combination of the compounds produces an overall effect that is greater than the sum of the individual elements.

Proliferative Disorder

This invention relates to a new combination therapy for proliferative disorders. Preferably, the composition of the invention is used for the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer.

It is especially preferred if the proliferative disorder is a mammary carcinoma. The composition or combination product of the invention can target specifically metastatic breast adenocarcinoma.

Composition or Combination Product of the Invention

The invention relies on the therapeutic combination of a compound of formula (I) and a compound of formula (X). The compound of formula (I) is

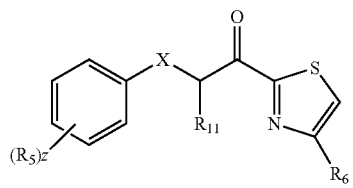

(I)

wherein X is O or S, preferably O
$R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$,
$R^{11}$ is H or $C_{1-6}$ alkyl;
each $R_5$ is —OC$_{1-10}$alkyl, —SC$_{1-10}$alkyl, —C$_{1-12}$alkyl, or OAr$^2$;
wherein Ar$^2$ is phenyl, optionally substituted with one or more halo;
each p is 0 to 3;
each z is 1 to 2;
or a salt thereof.
It is preferred if X is O.

It is preferred if $R_6$ is —COOC$_{1-6}$alkyl, or —CONHC$_{1-6}$alkyl, e.g. —COOC$_{1-2}$alkyl, or —CONHC$_{1-2}$alkyl.
It is preferred if $R^{11}$ is H or methyl, preferably H.
It is preferred if z is 1. It is preferred if p is 0.
It is preferred if the $R_5$ group is in the para position on the ring.
It is preferred if $R_5$ is —OC$_{4-10}$alkyl, —SC$_{4-10}$alkyl, —C$_{4-10}$alkyl, or OAr$^2$;
wherein Ar$^2$ is phenyl, optionally substituted with one halo. Halo means halogen and is preferably Cl or F, especially F.
More preferably, the compound of formula (I) is

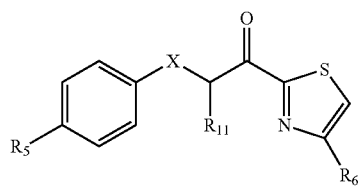

(II)

wherein X is O or S;
$R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$,
$R^{11}$ is H or $C_{1-6}$ alkyl;
$R_5$ is —OC$_{1-10}$alkyl, —SC$_{1-10}$alkyl, —C$_{1-12}$alkyl, or OAr$^2$;
Ar$^2$ is phenyl, optionally substituted with one or more halo;
each p is 0 to 3;
or a salt thereof.
More preferred compounds of the invention are those of formula (III):

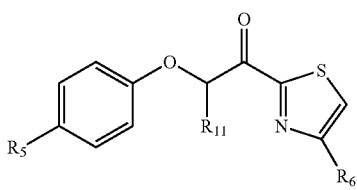

(III)

$R_6$ is —$(CH_2)_p$COOC$_{1-6}$alkyl, or —$(CH_2)_p$CONHC$_{1-6}$alkyl;
$R^{11}$ is H or methyl;
$R_5$ is —OC$_{1-10}$alkyl, —SC$_{1-10}$alkyl, —C$_{1-12}$alkyl, or OAr$^2$;
Ar$^2$ is phenyl, optionally substituted with one halo;
each p is 0 to 3;
or a salt thereof.
More preferred compounds of the invention are those of formula (IV):

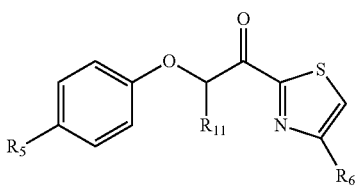

(IV)

$R_6$ is —COOC$_{1-6}$alkyl, or —CONHC$_{1-6}$alkyl;
$R^{11}$ is H or methyl;
$R_5$ is —OC$_{1-10}$alkyl, —SC$_{1-10}$alkyl, —C$_{1-12}$alkyl, or OAr$^2$;
Ar$^2$ is phenyl, optionally substituted with one halo;
or a salt thereof.
Preferred compounds are:

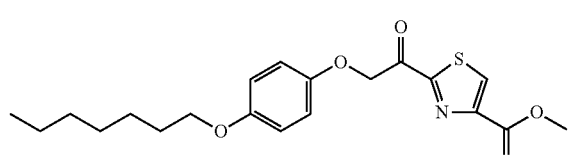

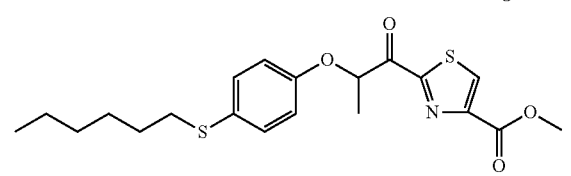

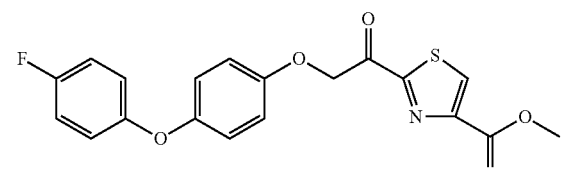

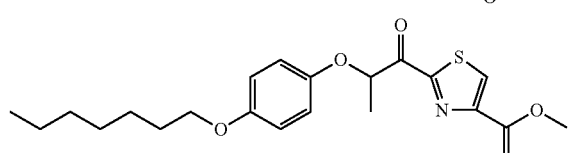

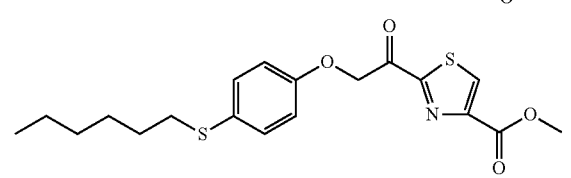

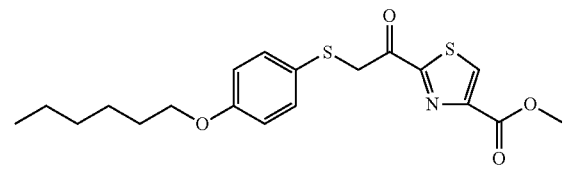

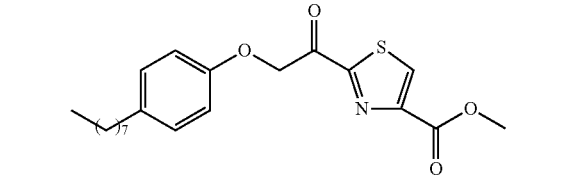

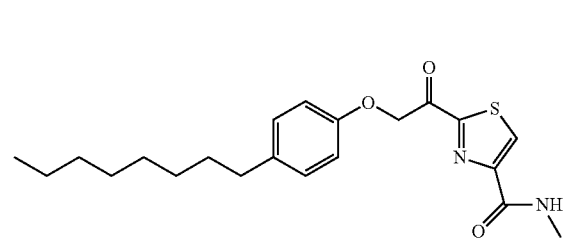

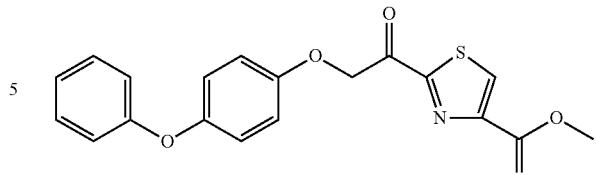

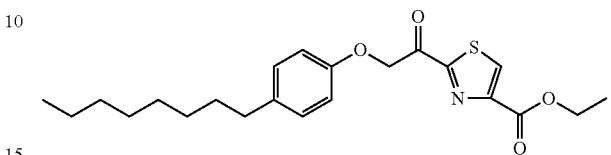

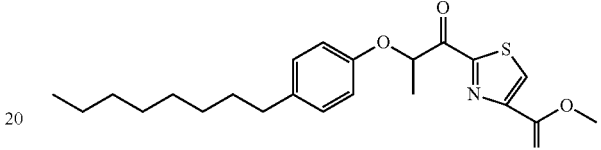

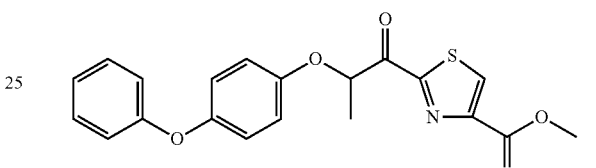

or salts thereof.
Especially preferred compounds are:

Compound 1

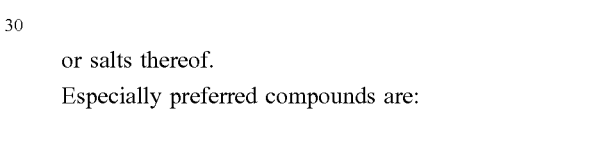

Compound 2

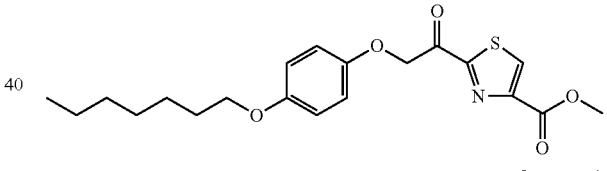

or a salt thereof.

The second component of the composition or product of the invention is a compound of formula (X) as hereinbefore defined. In compounds of formula (X) it is preferred if $R_1$ is phenyl wherein said phenyl is substituted by lower alkyl substituted by cyano.

It is preferred if $R_3$ is methyl. It is preferred if $R_4$ is unsubstituted quinolinyl. It is preferred if the quinoline group $R_4$ binds via its N containing ring, especially via its 3-position.

The compound of formula (X) is preferably of formula (XI)

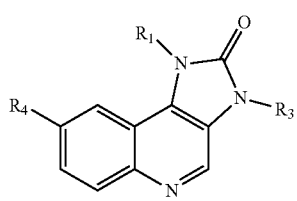

(XI)

where $R_1$ is phenyl wherein said phenyl is substituted by lower alkyl unsubstituted or substituted by cyano;
$R_3$ is methyl; and
$R_4$ is quinolinyl unsubstituted or substituted by halogen; or a salt thereof.

It is especially preferred if the compound (X) is 2-Methyl-[4-(3-methyl-2-oxo-8-quinolin-3-yl-2,3-dihydro-imidazo[4,5-c]quinolin-1-yl)-phenyl-propionitrile or a salt thereof such as toluene sulphonic acid salt thereof, i.e. the compound:

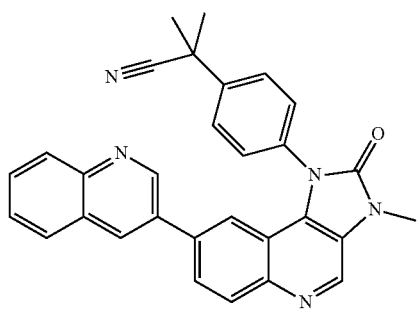 [SMILES: Cn1c(=O)n(-c2ccc(C(C)(C)C#N)cc2)c2c3cc(-c4cnc5ccccc5c4)ccc3ncc21]

or a salt thereof such as toluene sulphonic acid salt thereof. This compound is called BEZ235.

In a most preferred embodiment therefore the invention relates to a composition or combination product comprising compound 1 or 2:

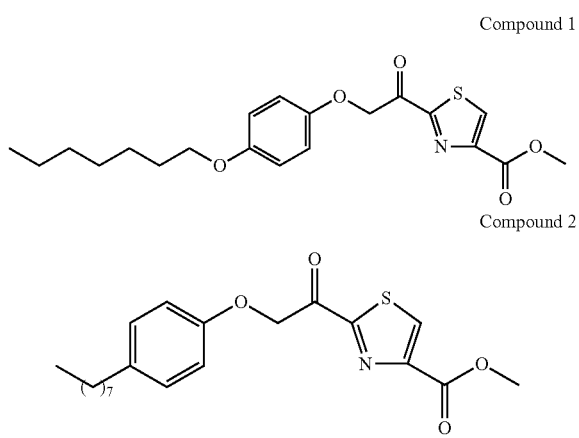

Compound 1

Compound 2 and BEZ235. Alternatively, another combination product of the invention is BEZ235, Compound 1 and Compound 2.

Where possible, the compounds of the invention can be administered in salt, hydrate or solvate form, especially salt form.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (X) and the resulting mixture evaporated to dryness (lyophilised) to obtain the acid addition salt as a solid. Alternatively, a compound of formula (X) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (e.g. methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Compounds of formula (I) may be manufactured using known chemical synthetic routes. Synthesis methods are outlined in WO2014/118195 and WO2011/039563 as well as references cited therein.

Synthesis methods for the preparation of compounds of formula (X) are described in EP-A-1888578 for example. Additional methods for assaying the activity of PI3K inhibitors, mTOR inhibitors and dual PI3K/mTOR inhibitors have been described. See WO2015/04939 and US Pat. Publication 2014/0066474, and Brana et al. (2012) *BMC Med.* 10:161, for example.

The weight ratio of the compounds of formula (I) to compounds of formula (X) in composition or combination product of the invention will be guided by intended use, the age and general health of the subject, and other parameters known to those of skill. For example, a particular weight ratio suitable for certain applications may be 10 to 90 wt % to 90 to 10 wt %, such as 30 to 70 wt % to 70 to 30 wt %.

More preferably, the amounts of each compound are determined in molar terms, and the ratio of each is 5:1 to 1:5 moles, such as 2:1 to 1:2 moles. Often, the compounds are used in an equimolar amount for certain applications The amount of the compounds of the invention in the composition will often be determined by the physician depending on the dosage required.

The composition or combination product of the invention is proposed primarily for use in the treatment or prevention of proliferative disorders such as cancer.

By treating or treatment is meant at least one of:
(i). inhibiting the disease i.e. arresting, reducing or delaying the development of the disease or a relapse thereof or at least one clinical or subclinical symptom thereof, or
(ii). relieving or attenuating one or more of the clinical or subclinical symptoms of the disease.

By prevention is meant (i) preventing or delaying the appearance of clinical symptoms of the disease developing in a mammal.

The benefit to a subject to be treated is either statistically significant or at least perceptible to the patient or to the physician. In general a skilled man can appreciate when "treatment" occurs. It is particularly preferred if the composition or combination product of the invention are used therapeutically, i.e. to treat a condition which has manifested rather than prophylactically. It may be that the composition or combination product of the invention is more effective when used therapeutically than prophylactically.

The composition or combination product of the invention can be used on any animal subject, in particular a mammal and more particularly to a human or an animal serving as a model for a disease (e.g., mouse, monkey, etc.).

In order to treat a disease an effective amount of the active composition or combination product needs to be administered to a patient. A "therapeutically effective amount" means the amount of a composition or combination product that, when administered to an animal for treating a state, disorder or condition, is sufficient to effect such treatment. The "therapeutically effective amount" will vary depending on the composition or combination product, the disease and its severity and the age, weight, physical condition and responsiveness of the subject to be treated and will be ultimately at the discretion of the attendant doctor.

It may be that to treat cancer according to the invention that the composition or combination product of the invention has to be re-administered at certain intervals. Suitable dosage regimes can be prescribed by a physician.

The composition or combination product of the invention typically comprises the active components in admixture with at least one pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of cancer.

It will be appreciated that pharmaceutical composition or combination products for use in accordance with the present invention may be in the form of oral, parenteral, transdermal, sublingual, topical, implant, nasal, or enterally administered (or other mucosally administered) suspensions, capsules or tablets, which may be formulated in conventional manner using one or more pharmaceutically acceptable carriers or excipients. The compositions of the invention could also be formulated as nanoparticle formulations.

However, for the treatment of cancer, the composition or combination product of the invention will preferably be administered orally or by parenteral or intravenous administration, such as injection. The composition or combination product may therefore be provided in the form of an tablet or solution for injection.

The pharmaceutical composition or combination product of the invention may contain from 0.01 to 99% weight-per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the present invention to administer the combination products described herein to a subject that has been exposed to, is being exposed to, or will be exposed to one or more anti-proliferative compounds and particularly those known to be used in many anti-cancer therapies. Non-limiting examples include aromatase inhibitors, anti-estrogens, topoisomerase I or II inhibitors microtubule active compounds, alkylating compounds, histone deacetylase inhibitors, and cyclooxygenase inhibitors such as those disclosed in WO2006/122806 and references cited therein6. Choice of whether to combine a combination product of the invention with one or more of the aforementioned anti-cancer therapies will be guided by recognized parameters known to those of skill in the field, including the particular type of cancer being treated, the age and health of the subject, etc.

The invention is described further below with reference to the following non-limiting examples and FIGURE.

DESCRIPTION OF FIGURES

FIG. 1 shows co-treatment with Compound 1 or compound 2 and BEZ235 shows synergistic effects on breast cancer cell viability compared to each inhibitor alone. Average and standard deviation of 4 experiments performed in 8 wells.

EXAMPLES

The following compounds were used in the Experiments:

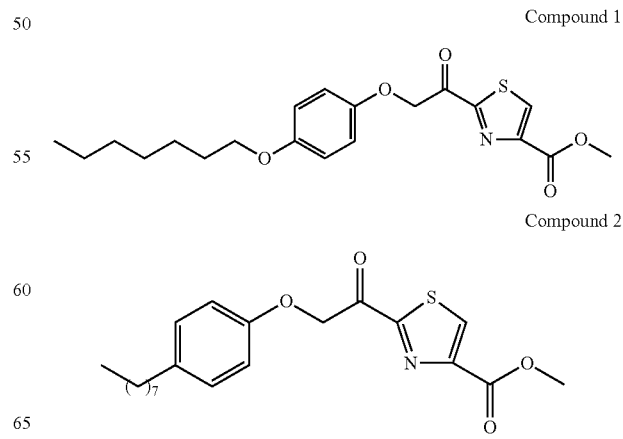

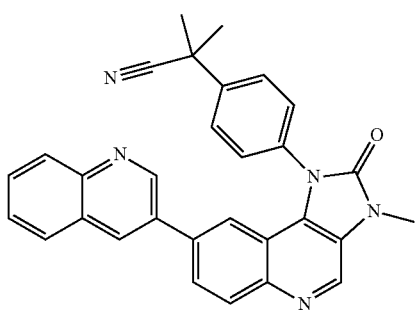
BEZ235

Methods

Cell Culture. The MDA-MB-468 cell line was from ATCC. This cell line was established from a pleural effusion of patient with metastatic breast adenocarcinoma. The cells were maintained in RPMI medium supplemented with 10% (v/v) FBS, 0.3 mg/mL L-glutamine, and 0.1 mg/mL gentamicin at 37° C. in 5% CO2. Sub-culture using trypsin-EDTA was performed every 3-4 days with a split ratio of 1:3-1:6 to ensure actively proliferating cells.

Resazurin Viability Assay. Cells were seeded in fully supplemented medium at a density of 7 000 cells per well in 96 well plates. After 24 hrs of cultivation, when the cells were ~60% confluent, the medium was replaced with serum free medium to ensure synchronization of the cells and to increase cell sensitivity to treatment. Following 16 hrs of serum starvation, the medium was replaced with fresh serum free medium with or without Compounds 1 and 2 (Avexxin, Norway), and NVP-BEZ235 (Cayman Chemicals, US) or solvent (DMSO, Sigma Aldrich, US). The cells were observed under the microscope to evaluate possible morphology changes and signs of stress before the addition of resazurin according to the manufacturers instructions (RnD Systems, UK). Resazurin was metabolized for 2 hrs (37° C., 5% CO2) before fluorescence was read at 544 nm excitation and 590 nm emission wavelengths (BioTek Synergy HT).

Results

Co-treatment with cPLA2α inhibitors and PI3K/mTOR inhibitor BEZ235 shows synergistic effects on breast cancer cell viability compared to each inhibitor alone. Initial experiments were performed to determine the effects of each inhibitor alone. All inhibitors were toxic to the cells at 25-100 μM, whereas at doses 1-5 μM, little or no signs of cellular stress of cytotoxicity were observed (results not shown). On this basis, combination treatment experiments were designed in which sub-toxic doses of the inhibitors were combined. Following 24 hrs of treatment, 5 μM of each inhibitor alone modestly reduced viability by 10-20%. For compound 2 and its derivative compound 1, the synergistic effect is pronounced. This observed trend of synergistic effects on cell viability, confirmed by microscopy, indicate potential beneficial effects of co-treatment of on cancer cell viability and proliferation (FIG. 1). The statistics are *p<0.05 vs ctrl, **p<0.005 vs Ctrl.

The invention claimed is:
1. A combination product comprising:
(A) Compound 1 or Compound 2 represented by one of the formulas below:

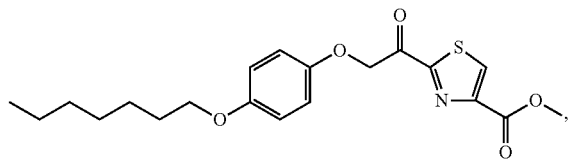
Compound 1 or

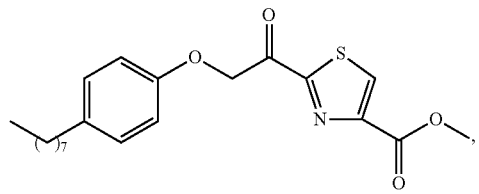
Compound 2 or a salt thereof; and
(B) BEZ235 represented by the formula below:

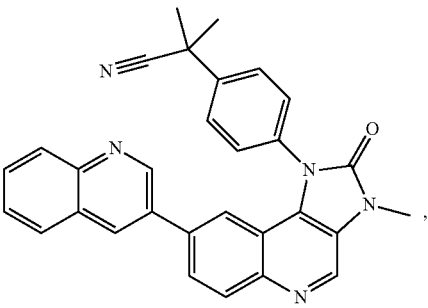 [SMILES: Cn1c(=O)n(-c2ccc(C(C)(C)C#N)cc2)c2c3cc(-c4cnc5ccccc5c4)ccc3ncc21]

or a salt thereof.
2. A pharmaceutical composition comprising:
(A) Compound 1 or Compound 2 represented by one of the formulas below:

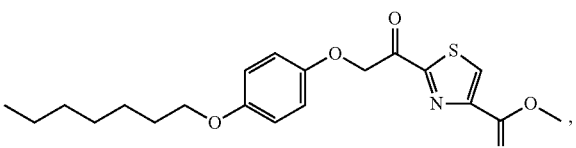
Compound 1 or

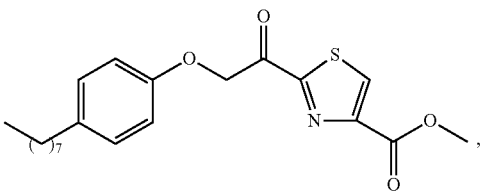
Compound 2 or a salt thereof;
(B) BEZ235 represented by the formula below:

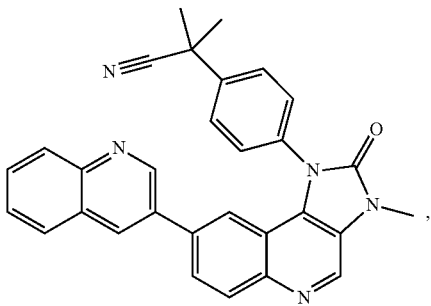 [SMILES: Cn1c(=O)n(-c2ccc(C(C)(C)C#N)cc2)c2c3cc(-c4cnc5ccccc5c4)ccc3ncc21]

or a salt thereof; and
a pharmaceutically acceptable diluent or carrier.

3. A pharmaceutical composition for simultaneous, sequential or separate use comprising a kit comprising a first composition comprising Compound 1 or Compound 2 as defined in claim 1 and a pharmaceutically-acceptable diluent or carrier, and a second composition comprising BEZ235 as defined in claim 1 and a pharmaceutically-acceptable diluent or carrier.

4. The pharmaceutical composition of claim 2 wherein the pharmaceutical composition is a fixed combination or non-fixed combination.

5. The pharmaceutical composition of claim 2, comprising (A) Compound 1, (B) BEZ235 or a salt thereof, and a pharmaceutically acceptable diluent or carrier.

6. The pharmaceutical composition of claim 2, comprising (A) Compound 2, (B) BEZ235 or a salt thereof, and a pharmaceutically acceptable diluent or carrier.

7. A method of treating cancer in a patient in need thereof comprising administering to said patient an effective amount of a pharmaceutical composition as claimed in claim 2, wherein the cancer is breast carcinoma.

8. A method of treating cancer in a patient in need thereof comprising administering to said patient an effective amount of Compound 1 or Compound 2 as defined in claim 2 and simultaneously, separately or sequentially administering to said patient BEZ235 or a salt thereof as defined in claim 2, wherein the cancer is breast carcinoma.

9. A method of treating cancer in a patient in need thereof comprising:
(i) identifying a patient who has received either one of Compound 1 and Compound 2, or BEZ235, as defined in claim 2 respectively;
(ii) administering to said patient an effective amount of either BEZ235, or one of Compound 1 and Compound 2, as defined in claim 2 so that said patient is administered with both Compound 1 and BEZ235, or both Compound 2 and BEZ235,
wherein the cancer is breast carcinoma.

* * * * *